US008691540B2

(12) United States Patent
Bramucci et al.

(10) Patent No.: US 8,691,540 B2
(45) Date of Patent: Apr. 8, 2014

(54) **BUTANOL DEHYDROGENASE ENZYME FROM THE BACTERIUM *ACHROMOBACTER XYLOSOXIDANS***

(75) Inventors: Michael G. Bramucci, Boothwyn, PA (US); Andrew C. Eliot, Wilmington, DE (US); Lori Ann Maggio-Hall, Wilmington, DE (US); Charles E. Nakamura, Claymont, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/479,643

(22) Filed: May 24, 2012

(65) Prior Publication Data

US 2012/0231515 A1 Sep. 13, 2012

Related U.S. Application Data

(63) Continuation of application No. 12/430,356, filed on Apr. 27, 2009, now Pat. No. 8,188,250.

(60) Provisional application No. 61/048,291, filed on Apr. 28, 2008.

(51) Int. Cl.
C12P 7/16 (2006.01)
C12N 9/04 (2006.01)
C12N 1/12 (2006.01)
C12N 1/13 (2006.01)
C12N 1/14 (2006.01)
C12N 1/21 (2006.01)
C12N 15/56 (2006.01)
C12N 1/18 (2006.01)
C12N 1/20 (2006.01)

(52) U.S. Cl.
CPC ... *C12P 7/16* (2013.01); *C12N 1/18* (2013.01); *C12N 1/20* (2013.01); *C12N 9/0006* (2013.01); *Y02E 50/10* (2013.01)
USPC ... 435/160; 435/190; 435/252.3; 435/252.31; 435/252.32; 435/252.33; 435/252.34; 435/254.11; 435/255.1; 435/255.4; 435/255.5; 435/255.6; 435/257.2; 536/23.2

(58) Field of Classification Search
None
See application file for complete search history.

(56) References Cited

U.S. PATENT DOCUMENTS

| | | | | |
|---|---|---|---|---|
| 5,198,345 | A * | 3/1993 | Gwynne et al. | 435/69.1 |
| 5,763,236 | A * | 6/1998 | Kojima et al. | 435/148 |
| 5,859,193 | A * | 1/1999 | Devare et al. | 530/350 |
| 6,358,717 | B1 * | 3/2002 | Blaschek et al. | 435/160 |
| 7,504,111 | B2 | 3/2009 | Fontana et al. | |
| 7,541,173 | B2 * | 6/2009 | Bramucci et al. | 435/252.3 |
| 7,659,104 | B2 * | 2/2010 | Bramucci et al. | 435/252.1 |
| 8,017,364 | B2 * | 9/2011 | Bramucci et al. | 435/160 |
| 8,188,250 | B2 * | 5/2012 | Bramucci et al. | 536/23.7 |
| 8,206,970 | B2 * | 6/2012 | Eliot et al. | 435/252.3 |
| 8,241,878 | B2 * | 8/2012 | Anthony et al. | 435/137 |
| 8,372,612 | B2 * | 2/2013 | Larossa et al. | 435/148 |
| 8,389,252 | B2 * | 3/2013 | LaRossa | 435/160 |
| 8,409,834 | B2 * | 4/2013 | Burlew et al. | 435/155 |
| 8,455,224 | B2 * | 6/2013 | Paul | 435/160 |
| 2002/0028492 | A1 * | 3/2002 | Lenke et al. | 435/155 |
| 2004/0157305 | A1 * | 8/2004 | Stampfer et al. | 435/189 |
| 2007/0092957 | A1 * | 4/2007 | Donaldson et al. | 435/157 |
| 2007/0259410 | A1 * | 11/2007 | Donaldson et al. | 435/148 |
| 2007/0292927 | A1 * | 12/2007 | Donaldson et al. | 435/160 |
| 2008/0015395 | A1 * | 1/2008 | D'amore et al. | 568/697 |
| 2008/0182308 | A1 | 7/2008 | Donaldson et al. | |
| 2008/0274522 | A1 * | 11/2008 | Bramucci et al. | 435/148 |
| 2008/0274524 | A1 * | 11/2008 | Bramucci et al. | 435/160 |
| 2008/0274525 | A1 * | 11/2008 | Bramucci et al. | 435/160 |
| 2008/0274526 | A1 * | 11/2008 | Bramucci et al. | 435/160 |
| 2009/0155870 | A1 * | 6/2009 | Donaldson et al. | 435/160 |
| 2009/0162911 | A1 * | 6/2009 | Larossa et al. | 435/148 |
| 2009/0203097 | A1 * | 8/2009 | Flint et al. | 435/160 |
| 2009/0239275 | A1 * | 9/2009 | Donaldson et al. | 435/160 |
| 2009/0303563 | A1 * | 12/2009 | Drabe et al. | 359/214.1 |
| 2009/0305369 | A1 * | 12/2009 | Donaldson et al. | 435/160 |
| 2009/0305370 | A1 * | 12/2009 | Grady et al. | 435/160 |
| 2010/0081179 | A1 * | 4/2010 | Anthony et al. | 435/135 |
| 2010/0081183 | A1 * | 4/2010 | Paul et al. | 435/160 |
| 2010/0093020 | A1 * | 4/2010 | Bramucci et al. | 435/34 |
| 2010/0167363 | A1 * | 7/2010 | Bramucci et al. | 435/160 |
| 2010/0167364 | A1 * | 7/2010 | Bramucci et al. | 435/160 |
| 2010/0167365 | A1 * | 7/2010 | Bramucci et al. | 435/160 |
| 2012/0015416 | A1 * | 1/2012 | Anthony et al. | 435/160 |

(Continued)

FOREIGN PATENT DOCUMENTS

JP 63017695 * 1/1998
WO 02/079243 * 10/2002

(Continued)

OTHER PUBLICATIONS

Cornman, R. S., et al., 2009, "Genomic analyses of the microsporidian *Nosema ceranae*, an emergent pathogen of honey bees", PLoS Pathogens, vol. 5, No. 6, p. E1000466.*

(Continued)

*Primary Examiner* — Manjunath Rao
*Assistant Examiner* — William W Moore
(74) *Attorney, Agent, or Firm* — Christine M. Lhulier

(57) ABSTRACT

From a bacterial strain isolated from an environmental sample, after enrichment in medium containing 1-butanol as the carbon source, a new enzyme with butanol dehydrogenase activity was identified. The enzyme can convert butyraldehyde to 1-butanol, isobutyraldehyde to isobutanol, as well as 2-butanone to 2-butanol and thus is useful for biosynthesis of butanol in recombinant microbial hosts producing these substrates. The encoding gene, named sadB, was isolated from the strain identified as an isolate of *Achromobacter xylosoxidans*.

5 Claims, No Drawings

(56) References Cited

U.S. PATENT DOCUMENTS

| | | | |
|---|---|---|---|
| 2012/0064585 A1* | 3/2012 | Anthony et al. | 435/137 |
| 2012/0149080 A1* | 6/2012 | Nagarajan et al. | 435/160 |
| 2012/0156735 A1* | 6/2012 | Dauner et al. | 435/115 |
| 2012/0196341 A1* | 8/2012 | Donaldson et al. | 435/160 |
| 2012/0237988 A1* | 9/2012 | Anthony et al. | 435/135 |
| 2012/0252084 A1* | 10/2012 | Anthony et al. | 435/160 |
| 2013/0040340 A1* | 2/2013 | Dauner et al. | 435/42 |
| 2013/0071898 A1* | 3/2013 | Anthony et al. | 435/146 |

FOREIGN PATENT DOCUMENTS

| | | | |
|---|---|---|---|
| WO | 2007041269 | * | 4/2007 |
| WO | 2007130518 | * | 11/2007 |
| WO | 2007130560 | * | 11/2007 |
| WO | 2007146377 | * | 12/2007 |

OTHER PUBLICATIONS

Accession No. NC003112, printed Aug. 13, 2009 and corresponding to GenBank Accession No. ACOL01003112.1; *Nosema ceranae* BRL01 Nc003112, whole genome shotgun sequence (last modification date Jun. 9, 2009) www.ncbi.nlm.nih.gov/nuccore/239601054.*
EMBL/UNIPROT Accession No. A9M046; printed Feb. 9, 2010, www.ebi.ac.uk/cgi-bin/dbfetch?db=emblcds&id=ABX73482 &style-raw.*
GenBank Accession No. CP000381.1, printed Aug. 12, 2010 (*Neisseria meningitidis* 053442, complete genome; last modification date Dec. 3, 2007); http://www.ncbi.nlm.nih.gov/nuccore/16594571?from=1313553 & to=1314593.*
GenBank Accession No. AAF41759, printed Aug. 13, 2009 (alcohol dehydrogenase, zinc-containing [*Neisseria meningitides* MC58]; last modification date May 26, 2005).*
International Search Report for PCT/US2009/041860, mailing date Dec. 17, 2009.*
Inui, M., et al., 2008, "Expression of Clostridium Butanol Synthetic Genes in *Escherichia coli*", Applied Microbiology Biotechnology, vol. 77, pp. 1305-1316.*
KEGG, *Neisseria meningitidis* 053442 (serogroup C): NMCC_I 310; XP-002556165 Reference listed in International Search Report from PCT/US2009/041869 mailed Dec. 17, 2009.*
Peng, J., et al., 2008, "Characterization of ST-4821 complex, a unique *Neisseria meningitidis* clone", Genomics, vol. 91, pp. 78-87.*
Atsumi, S., et al., 2008, "Metabolic engineering of *Escherichia coli* for 1-butanol production", Metabolic Engineering, vol. 10, pp. 305-311.*
Sirand-Pugnet, P. et al., 2007, "Being pathogenic, plastic, and sexual while living with a nearly minimal bacterial genome", PLoS Genetics, vol. 395, p. E75.*
Welch, R., et al., 1989, "Purification and characterization of the NADH-dependent butanol dehydrogenase from *Clostridium acetobutylicum* (ATCC 824)", Archives of Biochemistry and Biophysics, vol. 273, No. 2, pp. 309-318.*
Tettelin, H., et al., 2000, "Complete genome sequence of *Neisseria meningitidis* serogroup B strain MC58", Science, vol. 287, pp. 1809-1815.*
UniProtKB/TrEMBL Accession No. A5IY63, printed Aug. 17, 2009 (corresponding to GenBank Accession No. CU179680.1; *Mycoplasma agalactiae* PG2 chromosome, complete sequence; last modification date May 15, 2008). www.ncbi.nlm.nih.gov/nuc core/148291314?from=321091 &to=322137.*
Dickinson, J. R., et al., 1998, "An investigation of the metabolism of valine to isobutyl alcohol in *Saccharomyces cerevisiae*", The Journal of Biological Chemistry, vol. 273, No. 40, pp. 25751-25756.*
Garcia, A. I., et al., 1994, "Fusel alcohols production in beer fermentation processes", Process Biochemistry, vol. 29, pp. 303-309. Elsevier Science Limited.*
Girbal, L., et al., 1998, "Regulation of solvent production in *Clostridium acetobutylicum*", Trends in Biotechnology, vol. 16, pp. 11-16. Elsevier Science Ltd.*
Speranza, G., et al., 1997, "Conversion of meso-2,3-Butanediol into 2-Butanol by *Lactobacilli*. Stereochemical and enzymatic aspects", Journal of Agricultural and Food Chemistry, vol. 45, pp. 3476-3480. American Chemical Society.*
BLAST [online], 2010 [retrieved on Apr. 30, 2010]. Alignment of Accession No. 59395 [regional—Fontana et al.] and SEQ ID No. 2 [regional—this application] Retrieved from the Internet: URL: http://blast.ncbi.nlm.nih.gov./Blast.cgi>, pp. 1-3.*
Leskovac et al., "The three zinc-contianing alcohol dehydrogenases from baker's yeast, *Saccharomyces cerevisiae*," FEMS Yeast Research 2:481-94 (2002).
Li et al., "Crystal structure of a thermophilic alcohol dehydrogenase substrate complex suggests determinants of substrate specificity and thermostability," Proteins: Structure, Function, and Genetics 37:619-27 (1999).

* cited by examiner

SEQUENCE LISTING

```
<160> NUMBER OF SEQ ID NOS: 35

<210> SEQ ID NO 1
<211> LENGTH: 1047
<212> TYPE: DNA
<213> ORGANISM: Achromobacter xylosoxidans

<400> SEQUENCE: 1
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180 gaagggtag gcgtcatcga ggaagtgggc gagagtgtca cgcagttcaa gaaaggcgac     240
aaggtcctga tttcctgcgt cacttcttgc ggctcgtgcg actactgcaa gaagcagctt     300
tactcccatt gccgcgacgg cgggtggatc ctgggttaca tgatcgatgg cgtgcaggcc     360
gaatacgtcc gcatcccgca tgccgacaac agcctctaca agatccccca gacaattgac     420
gacgaaatcg ccgtcctgct gagcgacatc ctgcccaccg gccacgaaat cggcgtccag     480
```

```
tatgggaatg tccagccggg cgatgcggtg gctattgtcg gcgcgggccc cgtcggcatg    540
tccgtactgt tgaccgccca gttctactcc ccctcgacca tcatcgtgat cgacatggac    600
gagaatcgcc tccagctcgc caaggagctc ggggcaacgc acaccatcaa ctccggcacg    660
gagaacgttg tcgaagccgt gcataggatt gcggcagagg gagtcgatgt tgcgatcgag    720
gcggtgggca taccggcgac ttgggacatc tgccaggaga tcgtcaagcc cggcgcgcac    780
atcgccaacg tcggcgtgca tggcgtcaag gttgacttcg agattcagaa gctctggatc    840
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc   1020
atcctctcga acgcaggcgc tgcctga                                       1047

<210> SEQ ID NO 2
<211> LENGTH: 348
<212> TYPE: PRT
<213> ORGANISM: Achromobacter xylosoxidans

<400> SEQUENCE: 2

Met Lys Ala Leu Val Tyr His Gly Asp His Lys Ile Ser Leu Glu Asp
1               5                  10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
```

```
                    275                 280                 285
Leu Val Asn Thr Asn Thr Thr Pro Met Leu Met Lys Val Ala Ser Thr
            290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 3
<211> LENGTH: 1047
<212> TYPE: DNA
<213> ORGANISM: artificial sequence
<220> FEATURE:
<223> OTHER INFORMATION: codon optimized coding region

<400> SEQUENCE: 3
```

| | | | | | |
|---|---|---|---|---|---|
| atgaaggcat | tagtttatca | tgggatcac | aaaatttcgt | tagaagacaa | accaaaaccc | 60 |
| actctgcaga | aaccaacaga | cgttgtggtt | agggtgttga | aaacaacaat | ttgcggtact | 120 |
| gacttgggaa | tatacaaagg | taagaatcct | gaagtggcag | atggcagaat | cctgggtcat | 180 |
| gagggcgttg | gcgtcattga | agaagtgggc | gaatccgtga | cacaattcaa | aaagggggat | 240 |
| aaagttttaa | tctcctgcgt | tactagctgt | ggatcgtgtg | attattgcaa | gaagcaactg | 300 |
| tattcacact | gtagagacgg | tggctggatt | ttaggttaca | tgatcgacgg | tgtccaagcc | 360 |
| gaatacgtca | gaataccaca | tgctgacaat | tcattgtata | agatcccgca | aactatcgat | 420 |
| gatgaaattg | cagtactact | gtccgatatt | ttacctactg | gacatgaaat | tggtgttcaa | 480 |
| tatggtaacg | ttcaaccagg | cgatgctgta | gcaattgtag | gagcaggtcc | tgttggaatg | 540 |
| tcagttttgt | taactgctca | attttactcg | cctagtacca | ttattgttat | cgacatggac | 600 |
| gaaaaccgtt | tacaattagc | gaaggagctt | ggggccacac | acactattaa | ctccggtact | 660 |
| gaaaatgttg | tcgaagctgt | gcatcgtata | gcagccgaag | gagtggatgt | agcaatagaa | 720 |
| gctgttggta | taccegcaac | ctgggacatc | tgtcaggaaa | ttgtaaaacc | cggcgctcat | 780 |
| attgccaacg | tgggagttca | tggtgttaag | gtggactttg | aaattcaaaa | gttgtggatt | 840 |
| aagaatctaa | ccatcaccac | tggtttggtt | aacactaata | ctaccccaat | gttgatgaag | 900 |
| gtagcctcta | ctgataaatt | gcctttaaag | aaaatgatta | ctcacaggtt | tgagttagct | 960 |
| gaaatcgaac | acgcatatca | ggttttcttg | aatggcgcta | agaaaaagc | tatgaagatt | 1020 |
| attctatcta | atgcaggtgc | cgcctaa | | | | 1047 |

```
<210> SEQ ID NO 4
<211> LENGTH: 15
<212> TYPE: DNA
<213> ORGANISM: artificial sequence
<220> FEATURE:
<223> OTHER INFORMATION: primer

<400> SEQUENCE: 4
acgggcggtg tgtac                                                    15

<210> SEQ ID NO 5
<211> LENGTH: 16
<212> TYPE: DNA
<213> ORGANISM: artificial sequence
<220> FEATURE:
<223> OTHER INFORMATION: primer
```

<400> SEQUENCE: 5
gccagcagcc gcggta                                               16

<210> SEQ ID NO 6
<211> LENGTH: 1756
<212> TYPE: DNA
<213> ORGANISM: Achromobacter xylosoxidans

<400> SEQUENCE: 6
taggacgtgc aattgagatc agctcgaatc gatcgctctg atcgttccct acggtgtggc    60
acttctcaga tcaatgataa cgtctaaccc ctaccgaacg ccctgaggt ttgacgctat    120 cctcttcttc ggtcgtcacg tcgaatttca ctagcagtcc tctttgtaag caattaattg    180
acaaggtttg cgttgtggag ggaacttcac caactctcca cgaccgaagc ggacggacag    240
ccaggaggct ctgggtttct gtttctctga ggagcaaagc aaaattttt ggccccctta     300 ctcttttgtt tacgctcacc cagtcatgaa tcctaccgtg gtaatcgccc ccttgcggt     360 taggctaact acttctggta aaacccactc ccatggtgtg acgggcggtg tgtacaagac    420
ccgggaacgt attcaccgcg acatgctgat ccgcgattac tagcgattcc gacttcacgc    480
agtcgagttg cagactgcga tccggactac gatcgggttt ctgggattgg ctccccctcg    540
cgggttggcg accctctgtc ccgaccattg tatgacgtgt gaagcccta ccataagggc    600 catgaggact tgacgtcatc cccaccttcc tccggtttgt caccggcagt ctcattagag    660 tgcccttcg tagcaactaa tgacaagggt gcgctcgtt gcgggactta acccaacatc      720
tcacgacacg agctgacgac agccatgcag cacctgtgtt ccggttctct tgcgagcact    780
gccaaatctc ttcggcattc cagacatgtc aagggtaggt aagttttttc gcgttgcatc    840
gaattaatcc acatcatcca ccgcttgtgc gggtccccgt caattccttt gagttttaat    900
cttgcgaccg tactcccag gcggtcaact tcacgcgtta gctgcgctac caaggtccga     960
agaccccaac agctagttga catcgtttag ggcgtggact accagggtat ctaatcctgt   1020
ttgctcccca cgctttcgtg catgagcgtc agtgttatcc caggaggctg ccttcgccat   1080
cggtgttcct ccgcatatct acgcatttca ctgctacacg cggaattcca cctccctctg   1140
acacactcta gcccggtagt taaaaatgca gttccaaagt taagctctgg gatttcacat   1200 ctttcttcc gaaccgcctg cgcacgcttt acgcccagta attccgatta acgcttgcac    1260
cctacgtatt accgcggctg ctggcacgta gttagccggt gcttattctg caggtaccgt   1320
cagtttcgcg gggtattaac ccacgacgtt tctttcctgc caaaagtgct ttacaaccg   1380 aaggccttca tcgcacacgc gggatggctg gatcagggtt ccccccattg tccaaaattc   1440
cccactgctg cctcccgtag gagtctgggc cgtgtctcag tcccagtgtg ctggtcgtc   1500 ctctcaaacc agctacggat cgtcgccttg gtgagccgtt accccaccaa ctagctaatc   1560
cgatatcggc cgctccaata gtgcaaggtc ttgcgatccc ctgctttccc ccgtagggcg   1620
tatgcggtat tagctacgct ttcgcgtagt tatccccgc tactgggcac gttccgatac    1680
attactcacc cgttcgccac tcgccaccag accgaagtcc gtgctgccgt tcgactgcat   1740
gttaagctcc gctgcc                                                    1756

<210> SEQ ID NO 7
<211> LENGTH: 20
<212> TYPE: PRT
<213> ORGANISM: Achromobacter xylosoxidans

<400> SEQUENCE: 7

```
Met Lys Ala Leu Val Tyr His Gly Asp His Lys Ile Ser Leu Gly Asp
1               5                   10                  15

Lys Pro Lys Pro
            20

<210> SEQ ID NO 8
<211> LENGTH: 21
<212> TYPE: DNA
<213> ORGANISM: artificial sequence
<220> FEATURE:
<223> OTHER INFORMATION: degenerate primer
<220> FEATURE:
<221> NAME/KEY: misc_feature
<222> LOCATION: (12)..(12)
<223> OTHER INFORMATION: n = a, t, g, or c
<220> FEATURE:
<221> NAME/KEY: misc_feature
<222> LOCATION: (15)..(15)
<223> OTHER INFORMATION: n = a, t, g, or c
<220> FEATURE:
<221> NAME/KEY: misc_feature
<222> LOCATION: (18)..(18)
<223> OTHER INFORMATION: n = c or t
<220> FEATURE:
<221> NAME/KEY: misc_feature
<222> LOCATION: (21)..(21)
<223> OTHER INFORMATION: n = c or t

<400> SEQUENCE: 8
atgaaagctc tngtntanca n                                           21

<210> SEQ ID NO 9
<211> LENGTH: 29
<212> TYPE: DNA
<213> ORGANISM: artificial sequence
<220> FEATURE:
<223> OTHER INFORMATION: primer

<400> SEQUENCE: 9
ggatctcggc atctacaaag gcacgaatc                                   29

<210> SEQ ID NO 10
<211> LENGTH: 29
<212> TYPE: DNA
<213> ORGANISM: artificial sequence
<220> FEATURE:
<223> OTHER INFORMATION: primer

<400> SEQUENCE: 10
ggattcgtgc ctttgtagat gccgagatc                                   29

<210> SEQ ID NO 11
<211> LENGTH: 27
<212> TYPE: DNA
<213> ORGANISM: artificial sequence
<220> FEATURE:
<223> OTHER INFORMATION: primer

<400> SEQUENCE: 11
ccagtgttag gattgatgct gtctccg                                     27

<210> SEQ ID NO 12
<211> LENGTH: 24
<212> TYPE: DNA
<213> ORGANISM: artificial sequence
<220> FEATURE:
<223> OTHER INFORMATION: primer

<400> SEQUENCE: 12
```

```
ggtgtttcgt gctgcgcatt aacg                                          24

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
ggtgtttcgt gctgcgcatt aacg                                          24

<210> SEQ ID NO 14
<211> LENGTH: 30
<212> TYPE: DNA
<213> ORGANISM: artificial sequence
<220> FEATURE:
<223> OTHER INFORMATION: primer

<400> SEQUENCE: 14
catgaagggg taggcgtcat cgaggaagtg                                    30

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
gcttgaagac aagcccaagc                                               20

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
ggcaatggga gtaaagctgc                                               20

<210> SEQ ID NO 17
<211> LENGTH: 37
<212> TYPE: DNA
<213> ORGANISM: artificial sequence
<220> FEATURE:
<223> OTHER INFORMATION: primer

<400> SEQUENCE: 17
cctgatttcc tgcgtcactt cttgcggctc gtgcgac                            37

<210> SEQ ID NO 18
<211> LENGTH: 23
<212> TYPE: DNA
<213> ORGANISM: artificial sequence
<220> FEATURE:
<223> OTHER INFORMATION: primer

<400> SEQUENCE: 18
cgaacacgac gcccatgctg atg                                           23

<210> SEQ ID NO 19
<211> LENGTH: 22
<212> TYPE: DNA
<213> ORGANISM: artificial sequence
<220> FEATURE:
```

<223> OTHER INFORMATION: primer

<400> SEQUENCE: 19
ggacatctgc caggagatcg tc                                          22

<210> SEQ ID NO 20
<211> LENGTH: 23
<212> TYPE: DNA
<213> ORGANISM: artificial sequence
<220> FEATURE:
<223> OTHER INFORMATION: primer

<400> SEQUENCE: 20
caactccggc acggagaacg ttg                                         23

<210> SEQ ID NO 21
<211> LENGTH: 23
<212> TYPE: DNA
<213> ORGANISM: artificial sequence
<220> FEATURE:
<223> OTHER INFORMATION: primer

<400> SEQUENCE: 21
gcttctgaat ctcgaagtca acc                                         23

<210> SEQ ID NO 22
<211> LENGTH: 23
<212> TYPE: DNA
<213> ORGANISM: artificial sequence
<220> FEATURE:
<223> OTHER INFORMATION: primer

<400> SEQUENCE: 22
cgagctggag gcgattctcg tcc                                         23

<210> SEQ ID NO 23
<211> LENGTH: 28
<212> TYPE: DNA
<213> ORGANISM: artificial sequence
<220> FEATURE:
<223> OTHER INFORMATION: primer

<400> SEQUENCE: 23
gcgtccaggg cgtcaaagat caggcagc                                    28

<210> SEQ ID NO 24
<211> LENGTH: 30
<212> TYPE: DNA
<213> ORGANISM: artificial sequence
<220> FEATURE:
<223> OTHER INFORMATION: primer

<400> SEQUENCE: 24
ggaattcaca catgaaagct ctggtttatc                                  30

<210> SEQ ID NO 25
<211> LENGTH: 16
<212> TYPE: DNA
<213> ORGANISM: artificial sequence
<220> FEATURE:
<223> OTHER INFORMATION: primer

<400> SEQUENCE: 25
gtaaaacgac ggccag                                                 16

<210> SEQ ID NO 26

```
<211> LENGTH: 22
<212> TYPE: DNA
<213> ORGANISM: artificial sequence
<220> FEATURE:
<223> OTHER INFORMATION: primer

<400> SEQUENCE: 26
cacacaggaa acagctatga cc                                              22

<210> SEQ ID NO 27
<211> LENGTH: 55
<212> TYPE: DNA
<213> ORGANISM: artificial sequence
<220> FEATURE:
<223> OTHER INFORMATION: primer

<400> SEQUENCE: 27
aaacaaacac acatattaca atagctgagg atgaaagctc tggtttatca cggtg          55

<210> SEQ ID NO 28
<211> LENGTH: 55
<212> TYPE: DNA
<213> ORGANISM: artificial sequence
<220> FEATURE:
<223> OTHER INFORMATION: primer

<400> SEQUENCE: 28
atcataagaa attcgcttac tcttaattaa tcaggcagcg cctgcgttcg agagg          55

<210> SEQ ID NO 29
<211> LENGTH: 753
<212> TYPE: DNA
<213> ORGANISM: Saccharomyces cerevisiae

<400> SEQUENCE: 29
gcatgcttgc atttagtcgt gcaatgtatg actttaagat tgtgagcag  gaagaaaagg     60 gagaatcttc taacgataaa cccttgaaaa actgggtaga ctacgctatg ttgagttgct    120
acgcaggctg cacaattaca cgagaatgct cccgcctagg atttaaggct aagggacgtg    180
caatgcagac gacagatcta aatgaccgtg tcggtgaagt gttcgccaaa cttttcggtt    240
aacacatgca gtgatgcacg cgcgatggtg ctaagttaca tatatatata tatagccata    300
gtgatgtcta gtaacctttt atggtatatt tcttaatgtg gaaagatact agcgcgcgca    360
cccacacaca agcttcgtct tttcttgaag aaaagaggaa gctcgctaaa tgggattcca    420 cttttccgttc cctgccagct gatggaaaaa ggttagtgga acgatgaaga ataaaaagag    480
agatccactg aggtgaaatt tcagctgaca gcgagtttca tgatcgtgat gaacaatggt    540
aacgagttgt ggctgttgcc agggagggtg gttctcaact tttaatgtat ggccaaatcg    600
ctacttgggt ttgttatata acaaagaaga ataatgaac tgattctctt cctccttctt    660
gtcctttctt aattcgttg taattacctt cctttgtaat tttttttgta attattcttc    720
ttaataatcc aaacaaacac acatattaca ata                                 753

<210> SEQ ID NO 30
<211> LENGTH: 316
<212> TYPE: DNA
<213> ORGANISM: Saccharomyces cerevisiae

<400> SEQUENCE: 30
gagtaagcga atttcttatg atttatgatt tttattatta aataagttat aaaaaaaata     60
agtgtataca aatttttaaag tgactcttag gttttaaaac gaaaattctt attcttgagt    120
```

```
aactctttcc tgtaggtcag gttgctttct caggtatagc atgaggtcgc tcttattgac      180
cacacctcta ccggcatgcc gagcaaatgc ctgcaaatcg ctccccattt cacccaattg      240
tagatatgct aactccagca atgagttgat gaatctcggt gtgtatttta tgtcctcaga      300
ggacaacacc tgtggt                                                      316

<210> SEQ ID NO 31
<211> LENGTH: 1662
<212> TYPE: DNA
<213> ORGANISM: Lactococcus lactis

<400> SEQUENCE: 31
tctagacata tgtatactgt gggggattac ctgctggatc gcctgcacga actggggatt       60
gaagaaattt tcggtgtgcc aggcgattat aacctgcagt tcctggacca gattatctcg      120
cacaaagata tgaagtgggt cggtaacgcc aacgaactga acgcgagcta tggcagat        180 ggttatgccc gtaccaaaaa agctgctgcg tttctgacga cctttggcgt tggcgaactg      240
agcgccgtca acggactggc aggaagctac gccgagaacc tgccagttgt cgaaattgtt      300
gggtcgccta cttctaaggt tcagaatgaa ggcaaatttg tgcaccatac tctggctgat      360
ggggatttta acatttat gaaaatgcat gaaccggtta ctgcggcccg cacgctgctg        420
acagcagaga atgctacggt tgagatcgac gcgtcctgt ctgcgctgct gaaagagcgc       480
aagccggtat atatcaatct gcctgtcgat gttgccgcag cgaaagccga aaagccgtcg      540
ctgccactga aaaagaaaa cagcacctcc aatacatcgg accaggaaat tctgaataaa       600
atccaggaat cactgaagaa tgcgaagaaa ccgatcgtca tcaccggaca tgagatcatc      660
tcttttggcc tggaaaaaac ggtcacgcag ttcatttcta agaccaaact gcctatcacc      720
accctgaact tcggcaaatc tagcgtcgat gaagcgctgc cgagttttct gggtatctat      780
aatggtaccc tgtccgaacc gaacctgaaa gaattcgtcg aaagcgcgga ctttatcctg      840
atgctgggcg tgaaactgac ggatagctcc acaggcgcat ttacccacca tctgaacgag      900
aataaaatga tttccctgaa tatcgacgaa ggcaaaatct taacgagcg catccagaac       960 ttcgattttg aatctctgat tagttcgctg ctggatctgt ccgaaattga gtataaaggt     1020
aaatatattg ataaaaaaca ggaggatttt gtgccgtcta atgcgctgct gagtcaggat     1080
cgtctgtggc aagccgtaga aaacctgaca cagtctaatg aaacgattgt tgcggaacag     1140
ggaacttcat ttttcggcgc ctcatccatt tttctgaaat ccaaaagcca tttcattggc     1200
caaccgctgt gggggagtat tggttatacc tttccggcgg cgctgggttc acagattgca     1260
gataaggaat cacgccatct gctgtttatt ggtgacggca gcctgcagct gactgtccag     1320
gaactggggc tggcgatccg tgaaaaaatc aatccgattt gctttatcat caataacgac     1380
ggctacaccg tcgaacgcga aattcatgga ccgaatcaaa gttacaatga catcccgatg     1440
tggaactata gcaaactgcc ggaatccttt ggcgcgacag aggatcgcgt ggtgagtaaa     1500
attgtgcgta cggaaaacga atttgtgtcg gttatgaaag aagcgcaggc tgacccgaat     1560
cgcatgtatt ggattgaact gatcctggca aaagaaggcg caccgaaagt tctgaaaaag     1620 atgggaaac tgtttgcgga gcaaaataaa agctaaggat cc                         1662

<210> SEQ ID NO 32
<211> LENGTH: 28
<212> TYPE: DNA
<213> ORGANISM: artificial sequence
<220> FEATURE:
<223> OTHER INFORMATION: primer
```

-continued

```
<400> SEQUENCE: 32
ggatccgcat gcttgcattt agtcgtgc                                          28

<210> SEQ ID NO 33
<211> LENGTH: 20
<212> TYPE: DNA
<213> ORGANISM: artificial sequence
<220> FEATURE:
<223> OTHER INFORMATION: primer

<400> SEQUENCE: 33
gggatgcgga cgtattcggc                                                   20

<210> SEQ ID NO 34
<211> LENGTH: 39
<212> TYPE: DNA
<213> ORGANISM: artificial sequence
<220> FEATURE:
<223> OTHER INFORMATION: primer

<400> SEQUENCE: 34
cacacatatt acaatagcta gctgaggatg aaagctctg                              39

<210> SEQ ID NO 35
<211> LENGTH: 39
<212> TYPE: DNA
<213> ORGANISM: artificial sequence
<220> FEATURE:
<223> OTHER INFORMATION: primer

<400> SEQUENCE: 35
cagagctttc atcctcagct agctattgta atatgtgtg                              39
```

US 8,691,540 B2

BUTANOL DEHYDROGENASE ENZYME FROM THE BACTERIUM *ACHROMOBACTER XYLOSOXIDANS*

CROSS REFERENCE TO RELATED APPLICATIONS

This application is a continuation of and claims the benefit of priority of U.S. application Ser. No. 12/430,356, filed on Apr. 27, 2009, now U.S. Pat. No. 8,188,250, which is related to and claims the benefit of priority of U.S. Provisional Application No. 61/048,291, filed on Apr. 28, 2008. Each of the referenced applications is herein incorporated by reference.

FIELD OF THE INVENTION

The invention relates to the field of molecular biology and microbiology. More specifically, the field is related to butanol dehydrogenase enzymes useful for the production of butanol in microorganisms.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Microorganisms may be engineered for expression of biosynthetic pathways for production of butanols. Commonly owned and co-pending US Patent Application Publication US 20070092957 A1 discloses the engineering of recombinant microorganisms for production of isobutanol (2-methylpropan-1-ol). Commonly owned and co-pending US Patent Application Publication US20080182308A1 discloses the engineering of recombinant microorganisms for production of 1-butanol. Commonly owned and co-pending US Patent Application Publications US 20070259410A1 and US 20070292927A1 disclose the engineering of recombinant microorganisms for production of 2-butanol. Multiple pathways are described for biosynthesis of isobutanol and 2-butanol. The last step in all described pathways for all three products is the reduction of a more oxidized moiety to the alcohol moiety by an enzyme with butanol dehydrogenase activity. There are known alcohol dehydrogenases able to perform these conversions.

Additional enzymes with butanol dehydrogenase activity are desired for the production of butanols in recombinant host microorganisms engineered with a butanol biosynthetic pathway. Applicants have solved this problem by discovering an enzyme with butanol dehydrogenase activity in an environmental bacterial isolate, isolating the enzyme, and determining the encoding nucleic acid sequence from the identified *Achromobacter xylosoxidans* isolate.

SUMMARY OF THE INVENTION

Described herein is a new enzyme having butanol dehydrogenase activity, and the encoding isolated nucleic acid molecule.

The invention provides an isolated nucleic acid molecule comprising a first nucleotide sequence encoding a polypeptide of at least about 250 amino acids that has at least about 70% identity based on the Smith-Waterman method of alignment when compared to a polypeptide having the sequence as set forth in SEQ ID NO:2, or a second nucleotide sequence comprising the complement of the first nucleotide sequence, wherein said enzyme has butanol dehydrogenase activity.

In another aspect the invention provides an isolated nucleic acid molecule encoding a butanol dehydrogenase enzyme, selected from the group consisting of:
  a) an isolated nucleic acid molecule encoding the amino acid sequence as set forth in SEQ ID NO:2;
  b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; or
  an isolated nucleic acid molecule that is complementary to (a) or (b).

Additionally the invention provides polypeptides encoded by the described nucleic acid molecules as well as chimeric genes comprising the described nucleic acid molecules operably linked to at least one regulatory element, and transformed host cells containing the described nucleic acid molecules.

In one embodiment the invention provides a method for the production of 2-butanol comprising:
  (a) providing a recombinant microbial production host cell comprising the isolated nucleic acid molecule of the invention encoding a polypeptide having butanol dehydrogenase activity and a source of 2-butanone;
  b) growing the microbial host cell of (a) under conditions whereby the isolated nucleic acid molecule is expressed and the 2-butanone is converted to 2-butanol; and
  c) optionally recovering the 2-butanol.

In another embodiment the invention provides a method for the production of isobutanol comprising:
  a) providing a recombinant microbial production host cell comprising the isolated nucleic acid molecule of the invention encoding a polypeptide having butanol dehydrogenase activity and a source of isobutyraldehyde;
  b) growing the microbial host cell of (a) under conditions whereby the isolated nucleic acid molecule is expressed and the isobutyraldehyde is converted to isobutanol; and
  c) optionally recovering the isobutanol In another embodiment the invention provides a method for the production of 1-butanol comprising:
  a) providing a recombinant microbial production host cell comprising the isolated nucleic acid molecule of the invention encoding a polypeptide having butanol dehydrogenase activity and a source of butyraldehyde; and
  b) growing the microbial host cell of (a) under conditions whereby the isolated nucleic acid molecule is expressed and the butyraldehyde is converted to 1-butanol;
  c) and optionally recovering the 1-butanol.

Sequence Descriptions

The invention can be more fully understood from the following detailed description, figures and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the coding region identified for butanol dehydrogenase (sadB) from *Achromobacter xylosoxidans*.

SEQ ID NO:2 is the protein sequence for the identified butanol dehydrogenase from *Achromobacter xylosoxidans*.

SEQ ID NO:3 is a coding region for *Achromobacter xylosoxidans* butanol dehydrogenase that is codon-optimized for expression in *Saccharomyces cerevisiae*.

SEQ ID NOs:4 and 5 are primers for PCR amplification of strain BUTCON-5 16S rRNA.

SEQ ID NO:6 is the 16S rDNA sequence for strain BUTCON-5.

SEQ ID NO:7 is N-terminal peptide sequence of *A. xylosoxidans* butanol dehydrogenase.

SEQ ID NO:8 is the degenerate primer N331.

SEQ ID NOs:9-26 are sequencing primers for the *A. xylosoxidans* butanol dehydrogenase coding region. SEQ ID NOs:27 and 28 are primers for PCR amplification of the sadB coding region with extensions for gap repair cloning.

SEQ ID NO:29 is the yeast GPM promoter.

SEQ ID NO:30 is the yeast ADH1 terminator.

SEQ ID NO:31 is the *Lactococcus lactis* kivD coding region.

SEQ ID NOs:32 and 33 are sequencing primers for confirmation of pRS425::GPM-sadB.

SEQ ID NOs:34 and 35 are site directed mutagenesis primers for NheI site addition.

DETAILED DESCRIPTION OF THE INVENTION

Described herein is a new butanol dehydrogenase enzyme isolated from an environmental isolate of a bacterium identified as *Achromobacter xylosoxidans*. Provided in the invention are the amino acid sequence of this protein and proteins with at least about 70% amino acid identity and having butanol dehydrogenase activity. In addition, provided are isolated nucleic acid molecules encoding these proteins, which may be used in chimeric genes to express the butanol dehydrogenase enzyme in microorganisms. The *Achromobacter xylosoxidans* butanol dehydrogenase enzyme, and enzymes of related sequence, can be used for the production of 2-butanol from 2-butanone, isobutanol from isobutyraldehyde, or 1-butanol from butyraldehyde in a recombinant microorganism having a source of one of these substrates.

Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or combustion engines in vehicles.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 1-butanol, 2-butanol, isobutanol, or mixtures thereof.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual, 2$^{nd}$* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS*. 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, CABIOS. 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 70%, 75%, 80%, 85%, 90%, or 95%, or any integer percentage from 70% to 100% may be useful in describing the present invention, such as 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments encode polypeptides with the above identities and typically encode a polypeptide having at least about 250 amino acids, preferably at least 300 amino acids, and most preferably at least about 348 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular alcohol dehydrogenase proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The invention encompasses more than the specific exemplary sequences because it is well known in the art that alterations in an amino acid sequence or in a coding region wherein a chemically equivalent amino acid is substituted at a given site, which does not effect the functional properties of the encoded protein, are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Thus coding regions with the described codon variations, and proteins with the described amino acid variations are encompassed in the present invention.

As used herein the term "coding sequence" or "CDS" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

Butanol Dehydrogenase Activity of *Achromobacter xylosoxidans*

Through enriching an environmental sludge sample by serially culturing on medium containing 1-butanol, Applicants were able to isolate microorganisms that were capable of using 1-butanol as a sole carbon source. One isolate was identified by its 16S rRNA sequence as belonging to the bacterial species *Achromobacter xylosoxidans*. Applicants found in this isolate a butanol dehydrogenase enzyme activity which interconverted butyraldehyde and 1-butanol. Applicants also found that this butanol dehydrogenase enzyme activity also catalyzed the interconversion of isobutyraldehyde and isobutanol, as well as the interconversion of 2-butanone and 2-butanol. Surprisingly, this enzyme had kinetic constants for the alternate substrates comparable or superior to that for the 1-butanol substrate used in the enriching medium. These results indicated that this *Achromobacter xylosoxidans* butanol dehydrogenase may be used for production of 1-butanol, isobutanol, or 2-butanol in a recombinant microbial host cell having a source of the butyraldehyde, isobutyraldehyde or 2-butanone substrate, respectively.

Butanol Dehydrogenase Protein and Encoding Sequence

The nucleotide sequence identified in *Achromobacter xylosoxidans* that encodes an enzyme with butanol dehydrogenase activity (named sadB) is given as SEQ ID NO:1. The amino acid sequence of the full protein is given as SEQ ID NO:2. Comparison of this amino acid sequence to sequences in public databases revealed that this protein has surprisingly low similarity to known alcohol dehydrogenases. The most similar known sequences are 67% identical to the amino acid sequence of SEQ ID NO:2 over its length of 348 amino acids using BLAST with scoring matrix BLOSUM62, an expect cutoff of 10 and word size 3. A gap opening penalty of 11 and a gap extension of 1 were used. The closest similarities found were 67% amino acid identity to a Zn-containing alcohol dehydrogenase of *Neisseria meningitidis* MC58 (Accession #AAF41759.1) and 67% amino acid identity to the Zn-containing alcohol dehydrogenase of *Mycoplasma agalactiae* (Accession #A5IY63). Proteins having amino acid sequences that have greater than 67% identity to the sequence of the *Achromobacter xylosoxidans* butanol dehydrogenase (SEQ ID NO:2), that is identified and isolated herein, are proteins of the present invention. Proteins of the invention have amino acid sequences that are at least about 70%-75%, about 75%-80%, about 80%-85%, or about 85%-90% identical to SEQ ID NO:2, where about 90%-95% is more preferred. Most preferred are amino acid sequences that are at least about 95% identical to SEQ ID NO:2.

The nucleic acid sequence encoding the *Achromobacter xylosoxidans* butanol dehydrogenase (SEQ ID NO:1) has highest identity, which is about 65%, to the sequence encoding the *Neisseria meningitidis* MC58 Zn-containing alcohol dehydrogenase (Accession #NC003112), when compared to public sequences using BLAST with default parameters. Nucleic acid molecules of the present invention are those which encode polypeptides of at least about 250 amino acids and with butanol dehydrogenase activity, having at least about 70% identity to SEQ ID NO:2. The nucleic acid molecules may encode polypeptides of at least about 300 amino acids, or about 348 amino acids. The nucleic acid molecules may encode polypeptides with at least about 75%-80%, 80%-85%, 85%-90%, 90%-95%, or 95%-100% identity to SEQ ID NO:2.

Additional nucleic acid molecules of the present invention may be identified by hybridization to a nucleic acid molecule encoding a butanol dehydrogenase of SEQ ID NO:2 under the following conditions: 0.1×SSC, 0.1% SDS, 65° C. and washed with 2×SSC, 0.1% SDS followed by 0.1×SSC, 0.1% SDS. Nucleic acid molecules that are complementary to any of the above described nucleic acid molecules are additionally included in aspects of the present invention. Most suitable is a nucleic acid molecule encoding the polypeptide of SEQ ID NO:2, examples of which are SEQ ID NOs:1 and 3. Due to degeneracy of the genetic code, multiple nucleic acid sequences may encode the polypeptide of SEQ ID NO:2, as is well known to one skilled in the art. For example, the coding sequence may be codon-optimized for maximal expression in a specific host, such as the sequence codon-optimized for expression in *Saccharomyces cerevisiae* which is SEQ ID NO:3.

Isolation of Homologs

A nucleic acid molecule encoding the *Achromobacter xylosoxidans* butanol dehydrogenase, such as SEQ ID NO:1, may be used to isolate nucleic acid molecules encoding homologous proteins, that have at least 70%-75%, 75%-80%, 80%-85%, 85%-90%, 90%-95%, or 95%-100% sequence identity to this nucleic acid fragment, from the same or other microbial species. The encoded homologous proteins can be assessed for butanol dehydrogenase activity as described below. Isolation of homologs using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Natl. Acad. Sci. USA* 82, 1074, (1985; or strand displacement amplification (SDA), Walker, et al., *Proc. Natl. Acad. Sci. U.S.A.,* 89: 392, (1992)).

For example, nucleic acid fragments of the instant invention may be isolated directly by using all or a portion of the nucleic acid fragment of SEQ ID NO:1 as a DNA hybridization probe to screen libraries from any desired bacteria using methodology well known to those skilled in the art. Specific oligonucleotide probes based upon SEQ IND NO:1 can be designed and synthesized by methods known in the art (Maniatis, supra). Moreover, the sequence can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or the full-length of homologs of the SEQ ID NO:1. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33-50 IRL Press, Herndon, Va.); Rychlik, W. (1993) In White, B. A. (ed.), *Methods in Molecular Biology*, Vol. 15, pages 31-39, PCR Protocols: Current Methods and Applications. Humania Press, Inc., Totowa, N.J.)

Generally, two short segments of the instant nucleic acid sequence may be used to design primers for use in polymerase chain reaction protocols to amplify longer nucleic acid fragments encoding homologous coding regions from DNA or RNA. PCR may be performed using as template any DNA that contains a nucleic acid sequence homologous to SEQ ID NO:1, including for example, genomic DNA, cDNA or plasmid DNA as template. When using a library of cloned cDNA, the sequence of one primer is derived from SEQ ID NO:1, and the sequence of the other primer takes advantage of the presence of the polyadenylic acid tracts at the 3' end of the mRNA precursor encoding microbial genes. Alternatively, the second primer sequence may be based upon sequences derived from the cloning vector. For example, the skilled artisan can follow the RACE protocol using mRNA as template (Frohman et al., *Proc. Natl. Acad. Sci. USA* 85:8998 (1988)) to generate cDNAs by using PCR to amplify copies of the region between a single point in the transcript and the 3' or 5' end. Primers oriented in the 3' and 5' directions can be designed from the instant nucleic acid sequence. Using commercially available 3' RACE or 5' RACE systems (Life Technologies, Rockville, Md.), specific 3' or 5' cDNA fragments can be isolated (Ohara et al., *Proc. Natl. Acad. Sci. USA* 86:5673 (1989); Loh et al., *Science* 243:217 (1989)).

Alternatively a nucleic acid molecule of SEQ ID NO:1 or its complement may be employed as a hybridization reagent for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons (kD)), polyvinylpyrrolidone (about 250-500 kD), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In addition, since sequences of microbial genomes are rapidly becoming available to the public, homologs may be identified using bioinformatics approaches alone, which are well known to one skilled in the art.

Butanol Dehydrogenase Activity

Proteins of the invention have at least about 70% or greater amino acid identity to SEQ ID NO:2 and have butanol dehydrogenase activity. Nucleic acid molecules of the invention encode proteins with at least about 70% or greater amino acid identity to SEQ ID NO:2 having butanol dehydrogenase activity. One skilled in the art can readily assess butanol dehyrogenase activity in a protein. A protein is expressed in a microbial cell as described below and assayed for butanol dehydrogenase activity in cell extracts, crude enzyme preparations, or purified enzyme preparations. For example, assay of purified enzyme and crude enzyme preparations are described in Example 1 herein. An assay for 1-butanol dehydrogenase activity monitors the oxidation of NADH to NAD+ spectrophotometrically at 340 nm using appropriate amounts of enzyme in 50 mM potassium phosphate buffer, pH 6.2 at 35° C. containing 50 mM butyraldehyde and 0.2 mM NADH. An alternative assay with an alcohol substrate is performed at 35° C. in TRIS buffer, pH 8.5, containing 3 mM NAD$^+$ and varying concentrations of alcohol, or with a ketone or aldehyde substrate is performed at 35° C. with 50 mM MES buffer, pH 6.0, 200 µM NADH and varying concentrations of the ketone or aldehyde. Through these or other readily performable assays butanol dehydrogenase function is linked to structure of an identified protein encoded by an isolated nucleic acid molecule, both of which have an identified sequence.

Recombinant Expression

Nucleic acid fragments of the present invention may be expressed in microbial host cells, such as in bacteria, cyanobacteria, filamentous fungi and yeasts, resulting in expression of the encoded butanol dehydrogenase. Examples of host strains include but are not limited to *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Candida, Hansenula, Kluyveromyces* and *Saccharomyces*.

Microbial expression systems and expression vectors containing regulatory sequences that direct high level expression of foreign proteins are well known to those skilled in the art. Any of these may be used to construct chimeric genes for production of a protein encoded by a nucleic acid molecule of the present invention. These chimeric genes may then be introduced into appropriate microorganisms via transformation to provide high level expression of the enzyme.

Vectors useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). *E. coli*-yeast shuttle vectors are useful for cloning of chimeric genes for yeast expression. Typically the vector contains a selectable marker and sequences allowing autonomous replication or chromosomal integration in the desired host. In addition, suitable vectors may comprise a promoter region which harbors transcriptional initiation controls and a transcriptional termination control region, between which a coding region DNA fragment may be inserted, to provide expression of the inserted coding region. Both control regions may be derived from genes homologous to the transformed host cell, although it is to be understood that such control regions may also be derived from genes that are not native to the specific species chosen as a production host.

Initiation control regions or promoters which are useful to drive expression of the instant butanol dehydrogenase coding region in the desired host cell are numerous and familiar to those skilled in the art.

Suitable promoters include, but are not limited to, promoters derived from the following genes: CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); as well as the lac, ara, tet, trp, IPL, IPR, T7, tac, and trc promoters (useful for expression in *Escherichia coli, Alcaligenes*, and *Pseudomonas*); the amy, apr, and npr promoters, and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum* (Rud et al., *Microbiology* 152:1011-1019 (2006)).

Termination control regions may also be derived from various genes native to the preferred hosts. Optionally, a termination site may be unnecessary; however, it is most preferred if included.

Certain vectors are capable of replicating in a broad range of host bacteria and can be transferred by conjugation. The complete and annotated sequence of pRK404 and three related vectors: pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for heterologous gene expression in Gram-negative bacteria.

Some examples of vectors suitable for Gram-positive bacteria include pAMβ1 and derivatives thereof (Renault et al., *Gene* 183:175-182 (1996); and O'Sullivan et al., *Gene* 137: 227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimi-* crob. *Agents Chemother.* 38:1899-1903 (1994)). Several plasmids from *Lactobacillus plantarum* have also been reported (van Kranenburg et al., *Appl. Environ. Microbiol.* 71(3):1223-1230 (2005)).

Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with a chimeric gene encoding a butanol dehydrogenase of the present invention may be performed by either standard molecular cloning techniques in *E. coli* or by the gap repair recombination method in yeast. These vectors allow strain propagation in both *E. coli* and yeast strains.

Chimeric genes of the invention may be expressed from a stable replicating plasmid, or may be integrated into the host genome. Plasmids for DNA integration may include transposons, regions of nucleic acid sequence homologous to the integration target location in the host genome, or other sequences supporting integration. An additional type of vector may be a transposome produced using, for example, a system that is commercially available from EPICENTRE®. It is well known how to choose an appropriate vector for the desired target host and the desired function. In addition, a nucleic acid molecule encoding a butanol dehydrogenase of the invention may be integrated in an operably linked manner adjacent to an endogenous promoter in the host genome.

Butanol Microbial Production Hosts

Expression of an isolated nucleic acid molecule of the present invention provides the target transformed, recombinant microbial host cell with butanol dehydrogenase activity, whereby butanol is produced in the presence of butyraldehyde, isobutyraldehye, or 2-butanone. Each of these substrates may be produced naturally in a host cell, or produced as a product of an engineered biosynthetic pathway in the host cell. Bioysnthetic pathways that may be engineered in microorganisms for production of isobutanol, 2-butanol, or 1-butanol are described in US Patent Application Publications 20070092957 A1, 20070259410A1, 20070292927A1, and US20080182308A1, which are all herein incorporated by reference. With omission of the last step in each described pathway, the product is butyraldehyde, isobutyraldehyde, or 2-butanone. Thus a recombinant microbial host cell engineered with one of these described pathways lacking the last step has a source of butyraldehyde, isobutyraldehyde, or 2-butanone. Additional expression in the cell of an isolated nucleic acid molecule of the present invention results in the presence of butanol dehydrogease activity for conversion of butyraldehyde to 1-butanol, isobutyraldehyde to isobutanol, or 2-butanone to 2-butanol.

Growth for Butanol Production

Recombinant microbial production hosts comprising an isolated nucleic acid molecule of the invention and having butyraldehyde, isobutyraldehyde, or 2-butanone are grown in fermentation media which contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. Methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1-Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in commonly owned and co-pending U.S. Patent Application Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of an enzymatic pathway necessary for 2-butanone production.

Culture Conditions

Typically cells are grown at a temperature in the range of about 20° C. to about 40° C. in an appropriate medium. Suitable growth media in the present invention are common commercially prepared media such as Luria Bertani (LB) broth, Sabouraud Dextrose (SD) broth, Yeast Medium (YM) broth, or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation of yeast are between pH 5.0 to pH 9.0, where pH 6.0 to pH 8.0 is preferred as the initial condition. Suitable pH ranges for the fermentation of other microorganisms are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

Industrial Batch and Continuous Fermentations

Fermentation may be a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.* 36:227, (1992), herein incorporated by reference.

The fermentation culture may be adapted to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the turbidity of the culture medium, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that batch, fed-batch, continuous processes, or any known mode of fermentation is suitable for growth of the described recombinant microbial host cell. Additionally, it is contemplated that cells may be immobilized on a substrate as whole cell catalysts and subjected to fermentation conditions for 2-butanol production.

Methods for Butanol Isolation from the Fermentation Medium

The bioproduced butanol may be isolated from the fermentation medium using methods known in the art such as for ABE fermentations (see for example, Durre, *Appl. Microbiol. Biotechnol.* 49:639-648 (1998), Groot et al., *Process Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation.

Because butanol forms a low boiling point, azeotropic mixture with water, distillation can be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating a preferred embodiment of the invention, are given by way of illustration only. From the above discussion and these Examples, one skilled in the art can ascertain the essential characteristics of this invention, and, without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y., (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987) amd by *Methods in Yeast Genetics*, 2005, Cold Spring Harbor Laboratory Press, Cold Spring Harbor, N.Y.

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Microbial strains were obtained from The American Type Culture Collection (ATCC), Manassas, Va., unless otherwise noted.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometer(s), "mM" means millimolar, "µM" means micromolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography. The term "molar selectivity" is the number of moles of product produced per mole of sugar substrate consumed and is reported as a percent.

"$K_m$" is the concentration of substrate that results in a rate of product production equal to one-half of $V_{max}$ in an enzymatic reaction at a given concentration of enzyme.

"$V_{max}$" is the maximum rate of production of product in an enzymatic reaction at a given concentration of an enzyme. Typical units are micromoles of product per minute of reaction time.

Example 1

Isolation and Characterization of a Butanol Dehydrogenase from an Environmental Isolate of *Achromobacter xylosoxidans*

An enrichment process was used to determine whether it was possible to isolate microbes able to utilize 1-butanol as a sole carbon source from an environmental wastewater sludge sample. An enrichment culture was established by inoculating 1 mL of activated sludge into 10 mL of S12 medium (0.01 M ammonium sulfate, 0.05 M potassium phosphate, pH 7.0, 2 mM $MgCl_2$, 0.7 mM $CaCl_2$, 50 µM $MnCl_2$, 1 µM $FeCl_3$, 1 µM $ZnCl_2$, 1.72 µM $CuSO_4$, 2.53 µM $CoCl_2$, 2.42 µM $Na_2MoO_4$, 2 µM thiamine hydrochloride) containing yeast extract (0.001% final concentration) and 0.1% (w/v) 1-butanol in a 125 mL Erlenmeyer flask. The activated sludge was obtained from a DuPont wastewater treatment facility. The enrichment culture was incubated at 37° C. with reciprocal shaking. Initially, the culture was diluted every 1 to 2 days by replacing 9 mL of the culture with the same volume of medium. Subsequently, higher dilutions into the same medium containing 0.1-0.4% (w/v) initial 1-butanol concentration resulted in growth rates (34° C., 250 rpm) on the order of 0.55 $hr^{-1}$.

Samples (10 µL) of the enrichment culture were spread onto LB agar or Trypticase Soy agar and incubated at 35° C. for approximately 20 hours. Representative colonies were purified by streaking onto the same medium and incubating the cultures at 35° C. Isolates were selected for further examination. One isolate was named BUTCON-5. The identity of the BUTCON-5 strain was analyzed by rRNA characterization.

The 16S rRNA genes of strain BUTCON-5 were amplified by PCR and analyzed as follows. Strain BUTCON-5 was grown in LB for 16 hours at 37° C. with shaking. DNA was extracted from strain BUTCON-5 using the Ultraclean Microbial DNA Isolation Kit (MoBio, part #12224) according to the manufacturer's instructions. The 16S rRNA gene sequences were amplified by PCR by using a commercial kit according to the manufacturer's instructions (Perkin Elmer, Norwalk, Conn.) with primers JCR14 (ACGGGCGGTGTG-TAC; SEQ ID NO:4) and JCR15 (GCCAGCAGCCGCG-GTA; SEQ ID NO:5). PCR was performed in a Perkin Elmer GeneAmp 9600. The samples were incubated for 2 min at 94° C. and then cycled 30 times at 94° C. for 1 min, 55° C. for 1 min, and 72° C. for 1 min, with a 72° C. 5 min hold. The amplified 16S rRNA sequence fragment was purified using a commercial kit according to the manufacturer's instructions (QIAquick PCR Purification Kit, Valencia, Calif.) and sequenced on an automated ABI sequencer (Applied Biosystems, Foster City, Calif.). The sequencing reactions were initiated with primers JCR14 (SEQ ID NO:4) and JCR15 (SEQ ID NO:5). The 16S rRNA gene sequence was used as the query sequence for a BLAST search (Altschul, et al., *Nucleic Acids Res.* 25:3389-3402 (1997)) of available sequences in GenBank for similar sequences. The 16S rRNA gene sequence from strain BUTCON-5 (SEQ ID NO:6) had high sequence identity to several 16S rRNA gene sequences of bacteria belonging to the species *Achromobacter xylosoxidans*. The BUTCON-5 sequence had the highest identity (99%) to the 16S rRNA gene sequence isolated from *Achromobacter xylosoxidans* strain NFRI-A1 (GenBank Assession No. AB161691).

Purification of Butanol Dehydrogenase Activity from *A. xylosoxidans*

Purification of butanol dehydrogenase from the *Achromobacter xylosoxidans* BUTCON-5 strain was performed from 500 mL of an overnight culture of the strain grown in the medium described above. Cells were pelleted (Sorvall RC5B, F10 rotor, 6000 RPM, 20 minutes, 10° C.) and washed twice with 25 mL of 20 mM potassium phosphate, pH 7.0. The washed pellet was resuspended in 30 mL of 20 mM potassium phosphate, pH 7.0, and chilled on ice. The cells were lysed by sonication (Heat Systems Ultrasonics, Cell Disrupter model W375, Power level 50, Pulsed Mode, 70% duty cycle, 5 minutes). Cell free extract was prepared by centrifuging the lysate (Sorvall RC5B, SS34 rotor, 18000 RPM, 20 minutes, 10° C.). The supernatant was stored in aliquots at −80° C. Two aliqouts (9.12 mL) were thawed, combined and subjected to protamine sulfate precipitation. Four dropwise additions of 100 μL each of a 50 mg/mL protamine sulfate solution were made (total 15% w/w to protein) over 15 minutes. The precipitate was removed by centrifugation (Beckman refrigerated microfuge, 20,000 RCF, 4° C., 10 minutes).

A Superdex prep 200 column was equilibrated with 20 mM potassium phosphate, 20 mM KCl, pH 7.0. The supernatant from the protamine sulfate precipitation was concentrated to about 1.3 mL with a Centriprep concentrator, loaded onto the column and eluted isocratically at 1.00 mL/min with the same buffer. The fractions were collected and assayed for 1-butanol dehydrogenase activity. The assay monitored the oxidation of NADH to NAD$^+$ spectrophotometrically at 340 nm using appropriate amounts of enzyme in 50 mM potassium phosphate buffer, pH 6.2 at 35° C. containing 50 mM butyraldehyde and 0.2 mM NADH. Fractions with high specific activity were pooled and concentrated to give a highly purified fraction with specific activity of 19 μmol/min/mg protein.

Activity Stains of Isolated Butanol Dehydrogenase from *A. xylosoxidans*

The purified enzyme and molecular weight standards were subjected to electrophoresis using non-denaturing polyacrylamide gels (8-16% Tris-Glycine gradient gel, Invitrogen). After electrophoresis, the gels were removed and stained for protein (Simply Blue Protein Stain, Invitrogen) or stained for activity by coupling the conversion of 1-butanol plus NAD$^+$ to butyraldehyde plus NADH with the conversion of 3 [4,5-dimethylthiazol-2-yl]-2,5-diphenyltetrazolium bromide (MTT) to a deeply colored formazan, using phenazine methosulfate (PMS) as mediator (Tang et al., et al., J. Bacteriol. 140, 182 (1997)). The activity solution contained 0.5 mg PMS, 5 mg MTT, 20 mg NAD$^+$ and 1 mL of 1-butanol in a total volume of 25 mL. The resulting activity stain migrated with a band intermediate between the B-phycoerythrin (242 k dalton) and lactate dehydrogenase (146 k dalton) protein standards. Subsequent activity staining using 2-butanol (producing 2-butanone) or isobutanol (producing isobutryaldehyde) produced a band with identical molecular weight, indicating that the same protein was active on these butanol isomers.

Kinetic Characterization of Butanol Dehydrogenase from *A. xylosoxidans*

The kinetic parameters of the *A. xylosoxidans* butanol dehydrogenase were determined with 1-butanol, 2-butanol, butyraldehyde, 2-butanone (methyl ethyl ketone), and isobutyraldehyde as substrates for reduction (ketones and aldehydes) or oxidation (alcohols). Reactions with alcohol substrates were performed at 35° C. in TRIS buffer, pH 8.5, containing 3 mM NAD$^+$ and varying concentrations of alcohol. Reactions with ketone or aldehyde substrates were performed at 35° C. with 50 mM MES buffer, pH 6.0, 200 μM NADH and varying concentrations of the ketone or aldehyde. Crude enzyme preparations were used, obtained either from *A. xylosoxidans* or recombinant *E. coli* strain Mach1/pTrc99a::sadB (described in Example 3 below). The $V_{max}$ and $K_m$ for each substrate was calculated from the results and these are given in Table 1.

TABLE 1

Kinetic constants of *A. xylosoxidans* butanol dehydrogenase.

| Substrate | $V_{max}$, μmol/min | $K_m$, mM | Enzyme Source |
|---|---|---|---|
| 1-Butanol | 0.02 | 4.6 | *A. xylosoxidans* |
| 2-Butanol | 0.22 | 0.3 | *A. xylosoxidans* |
| Butyraldehyde | 0.67 | 7.3 | *A. xylosoxidans* |
| 2-Butanone | 0.35 | 0.5 | *A. xylosoxidans* |
| Isobutyraldehyde | 1.1 | 1.9 | *E. coli* strain Mach1/pTrc99a |

Example 2

Obtaining the Coding Sequence for the Butanol Dehydrogenase of *Achromobacter xylosoxidans*

A band corresponding to the appropriate molecular weight of the *A. xylosidans* butanol dehydrogenase was excised from a gel prepared as described in Example 1, the protein was isolated and the N-terminal sequence was determined using standard methods. The sequence was determined to be MKALVYHGDHKISLGDKPKP (SEQ ID NO:7).

Sequencing primers were designed from projected DNA sequences encoding this peptide. The degenerate primer N331 (SEQ ID NO:8) was successful in providing the first sequence information in the following experiment. Genomic DNA was prepared from *Achromobacter xylosoxidans* strain BUTCON-5 using a Gentra Puregene kit (Gentra Systems, Inc., Minneapolis, Minn.; catalog number D-5500A) following the recommended protocol for gram negative organisms. Initially, a modified protocol for sequencing from purified genomic DNA (gDNA) was used to walk along the chromosome from the 5' end toward the 3' end of the coding region. For each sequencing primer reaction, 20 μl of purified gDNA (~200 ng/μl) was added to 16 μl BigDye v3.1 Sequencing Reagent (Applied Biosystems Cat. No. 4337457), 3 μl of 10 μM primer, and 1 μl DMSO (Sigma-Aldrich Cat. No. D8418). The sequencing reactions were then thermal cycled as follows: 3 min. at 96° C. followed by 200 cycles of (95° C. 30 sec+55° C. 20 sec+60° C. 2 min) then stored at 4° C. The unincorporated ddNTPs were removed prior to sequencing using Edge Biosystems (Gaithersburg, Md. 20877, USA) clean-up plates. For each sequencing reaction the total 40 μl was pipetted into one well of a pre-spun 96-well clean up plate. The plate was then spun for 5 min at 5,000×g in a Sorvall RT-7 refrigerated centrifuge. The cleaned up reactions were then placed directly onto an Applied Biosystems 3730 DNA sequencer and sequenced with automatic base calling.

Sequence obtained with degenerate primer N331 was analyzed by BLASTX searching of publicly available sequences and was found to have 65% similarity of the encoded amino acid to a *Neisseria meningitidis* Zn-dependant alcohol dehydrogenase and similarity to proteins with related activity from other organisms, to a lesser degree. Additional primers were prepared from the sequence obtained with primer N331 and a second round of sequencing was carried out. The results obtained from primers N401 (forward; SEQ ID NO:9), $N_4O_2$ (reverse; SEQ ID NO:10) and N406 (forward; SEQ ID NO:11) revealed the start codon and a putative zinc-binding cys-X-X-cys-X-X-cys motif. Additional forward and reverse sequencing primers were designed from the newly obtained sequence. Sequencing results from primer N412 (SEQ ID NO:12), N421 (SEQ ID NO:13) and N422 (SEQ ID NO:14) overlapped with that obtained from primers N331 and $N_4O_2$, enabling the assembly of a 426 nt contig.

GenomiPhi (GE Healthcare Cat. No. 25-6600-01) was then used to amplify gDNA to improve sequencing read lengths, as follows. One nanogram of purified gDNA was added to 9 µl Sample Buffer and heated at 95° C. for 3 min followed by cooling to 4° C. 10 µl of Enzyme Mix consisting of 9 µl reaction buffer+1 µl enzyme was added to each cooled sample and the mixture was incubated for 18 hrs at 30° C. The enzyme was subsequently inactivated by heating to 65° C. for 10 minutes. The samples were stored at 4° C. until sequenced. For each sequencing primer reaction, 8 µl of amplified DNA was and added to 8 µl BigDye v3.1 Sequencing reagent (Applied Biosystems Cat. No. 4337457), 4µ 5×Sequencing Buffer (Applied Biosystems, 4336699), 3 µl of 10 µM primer, and 16 µl Molecular Biology Grade water (Mediatech, Inc.), and 1 µl DMSO (Sigma-Aldrich Cat. No. D8418).

Sequencing of the amplified DNA with primers N462 (SEQ ID NO:17), N464 (SEQ ID NO:19) and N465 (SEQ ID NO:20), all prepared from the 426 nt contig sequence, completed the 3' end of the coding region and enabled assembly of a 1047 nt open reading frame. For final verification, forward and reverse primers N473 (SEQ ID NO:24) and N469 (SEQ ID NO:23), respectively, were designed from the "rough" contig assembly to PCR amplify the entire coding sequence from purified gDNA using the high-fidelity Phusion™ amplification kit (New England Biolabs Cat. No. F-531S). The PCR product was TOPO-Blunt cloned into pCR4 BLUNT (Invitrogen Cat. No. K2835-20) to produce pCR4Blunt:: sadB, which was transformed into *E. coli* Mach-1 cells (provided in the kit) according to the manufacturer's protocol. Plasmid was subsequently isolated from four clones, and the inserts were sequenced with flanking vector-specific primers (M13 forward and reverse; SEQ ID NOs:25, 26) and primers N456 (SEQ ID NO:15), N457 (SEQ ID NO:16), N462 (SEQ ID NO:17), N463 (SEQ ID NO:18), N465 (SEQ ID NO:20), N466 (SEQ ID NO:21), and N467 (SEQ ID NO:22) which are coding sequence insert-specific. At least 4× coverage was achieved which verified the 1047 nt coding region sequence (SEQ ID NO:1).

The gene encoding the identified butanol dehydrogenase of *A. xylosoxidans* was named sadB for secondary alcohol dehydrogenase-2-butanol. The enzyme was shown to have broader substrates than the 2-butanol secondary alcohol including 1-butanol and isobutanol, shown in Example 1, making it a butanol dehydrogenase. The protein (SEQ ID NO:2) translated from the final 1047 nt coding sequence was used in a BLASTP query of publicly available sequences using default parameters. It was found to be most similar to a putative Zn-dependant alcohol dehydrogenase from *Neisseria meningitidis* (Genbank Accession No. AAF41759), which is 67% identical to the sadB amino acid sequence. The DNA coding sequence for the *Achromobacter xylosoxidans* butanol dehydrogenase was found by BLAST analysis of publicly available sequences to have 64.5% identity to the coding sequence of the *Neisseria meningitidis* MC58 Zn-dependant alcohol dehydrogenase (Genbank Accession No. NC003112).

Example 3

*E. coli* Construct for Expression of *Achromobacter xylosoxidans* Alcohol Dehydrogenase for Conversion of 2-butanone to 2-butanol The secondary alcohol dehydrogenase (sadB) from *Achromobacter xylosoxidans* was cloned into the vector pTrc99a (Amann et al., *Gene* 69(2):301-315 (1988)). The coding region (SEQ ID NO:1) was amplified using standard conditions from *A. xylosoxidans* genomic DNA, prepared using a Gentra Puregene kit (Gentra Systems, Inc., Minneapolis, Minn.; catalog number D-5500A) following the recommended protocol for gram negative organisms using forward and reverse primers N473 and N469 (SEQ ID NOs:24 and 23). The PCR product was TOPO-Blunt cloned into pCR4 BLUNT (Invitrogen) to produce pCR4Blunt::sadB, which was used to transform *E. coli* Mach-1 cells. Plasmid DNA was subsequently isolated from four clones, and the sequence verified. The plasmid was then digested with EcoRI, releasing the sadB fragment, which was ligated with EcoRI-digested pTrc99a to generate pTrc99a::sadB. The *E. coli* Mach 1 cells were transformed with the plasmid and the resulting transformant was named Mach1/pTrc99a::sadB. Activity of the enzyme expressed from the sadB gene in these cells was assayed and the results were given in Table 1 in Example 1.

Example 4

Yeast Expressing Butanol Dehydrogenase Encoded by sadB Construction of pRS425::GPM-sadB The sadB gene coding region was PCR amplified from pCR4Blunt::sadB. The PCR primers N583 and N584 (SEQ ID NOs:27 and 28) contained additional 5' sequences that overlapped with the yeast GPM promoter (SEQ ID NO:29) and the ADH1 terminator (SEQ ID NO:30). The PCR product was then cloned using "gap repair" methodology in *Saccharomyces cerevisiae* (Ma et al. ibid) into the yeast-*E. coli* shuttle vector pRS425::GPM::kivD::ADH as follows. This vector contains a chimeric gene including the yeast GPM promoter (SEQ ID NO:29), the *Lactococcus lactis* kivD coding region (SEQ ID NO:31), and the ADH1 terminator (SEQ ID NO:30) in the pRS425 vector (from the pRS400 series: Christianson et al. *Gene* 110:119-122 (1992)) and was described in commonly owned and co-pending US Patent Application Publication #20070092957 A1, Example 17). The vector was digested with BbvCI and PacI restriction enzymes to release the kivD coding region. Approximately 1 µg of the remaining vector fragment was used to transform *S. cerevisiae* strain BY4741 along with 1 µg of the sadB PCR product. Transformants were selected on synthetic complete medium lacking leucine. The proper recombination event, generating pRS425::GPM-sadB, was confirmed by PCR using primers N142 and N459 (SEQ ID NOs:32 and 33).

Three clones were cultured in synthetic complete medium lacking leucine to generate cells for assays. Cell free extracts were prepared by standard bead beating method using 1 ml of 0.5 mm beads and 1.5 ml of yeast cell suspension. The activity, assayed as MEK reductase activity, was measured as follows. Yeast cell free extract (a sample of 50 µl and one of 100 µl as noted in Table 2) was added to a quartz cuvette containing 920 or 870 µl of 50 mM MES buffer (pH 6), 10 µl of 20 mM NADH, and 10 µl of 100 mM DTT. The absorbance at 340 nm was monitored for 1 minute to obtain the background rate before adding 10 μl of 500 mM 2-butanone to the reaction. The absorbance at 340 nm was monitored for an additional 2 minutes to obtain the reaction rate. All three clones contained significant MEK reduction activity compared to the vector-only control (BY4741/pRS426) as shown by the activities (in μmole/min/mg) reported in Table 2.

TABLE 2

Activity of *A. xylosoxidans* butanol dehydrogenase expressed in yeast.

| Strain | Volume of yeast extract assayed (μl) | MEK reductase Activity (μmole/min/mg) |
| --- | --- | --- |
| BY4741/pRS426 | 50 | 0.0014 |
|  | 100 | 0.0000 |
| BY4741/pRS425::GPM-sadB #1 | 50 | 0.1866 |
|  | 100 | 0.3056 |
| BY4741/pRS425::GPM-sadB #2 | 50 | 0.1944 |
|  | 100 | 0.3075 |
| BY4741/pRS425::GPM-sadB #3 | 50 | 0.1249 |
|  | 100 | 0.2578 |

Example 5

Expression of Codon Optimized sadB in *S. cerevisiae*

The sequence encoding the *A. xylosoxidans* butanol dehydrogenase was codon optimized for expression in *Saccharomyces cerevisiae*, using standard codon usage information as reported in the Codon Usage Database maintained by Kazusa DNA Research Institute (Japan), by DNA 2.0 (Menlo Park, Calif.). A cloned DNA fragment containing the optimized coding region called sadBy (SEQ ID NO:3) was received from DNA 2.0. A chimeric gene containing the GPM promoter-sadBy coding region-ADH/terminator was constructed as follows.

Site directed mutagenesis with primers OT1074 and OT1075 (SEQ ID NOs:34 and 35) was used to generate a NheI restriction site upstream of the ATG codon of the sadB coding region in pRS425::GPM-sadB, which was described in Example 4, creating vector pRS425::GPMp-sadB(NheI)-ADH1t. The codon-optimized sadBy fragment was subcloned into pRS425::GPMp-sadB(NheI)-ADH1t using NheI and PacI restriction sites, replacing the original sadB coding region. The resulting plasmid was called pRS425::GPMp-sadBy-ADH1t.

*S. cerevisiae* BY4741 (ATCC #201388) was transformed with plasmid pRS425-GPMp-sadBy-ADH1t using standard genetic techniques (Methods in Yeast Genetics, 2005, Cold Spring Harbor Laboratory Press, Cold Spring Harbor, N.Y., pp. 201-202) and transformants were selected on synthetic complete media lacking leucine and supplemented with 2% glucose at 30° C. BY4741 pRS425::GPMp-sadBy-ADH1t was grown in synthetic complete media lacking leucine and supplemented with 2% glucose at 30° C. overnight, and inoculated into 200 ml of the same media to a final OD600 of 0.2. The culture was incubated at 30° C. shaking at 220 rpm until being harvested by centrifugation at an OD600 of 0.8-1.0 and stored at −80° C.

Yeast extracts were prepared as described above in Example 4. Activity assays for 2-butanone reduction were performed as described above in Example 4. Specific activities (μmole/min/mg) from individual assays are provided in Table 3.

TABLE 3

Activity of *A. xylosoxidans* butanol dehydrogenase expressed in yeast with codon optimized coding region.

| Sample | Specific activity |
| --- | --- |
| BY4741 pRS425::GPMp-sadBy-ADH1t Clone A (50 μl) | 0.174 |
| BY4741 pRS425::GPMp-sadBy-ADH1tCLone B (50 μl) | 0.253 |
| BY4741 pRS425::GPMp-sadBy-ADH1t Clone A (100 μl) | 0.118 |
| BY4741 pRS425::GPMp-sadBy-ADH1t Clone B (100 μl) | 0.192 |
| Average | 0.184* |

*St. dev. = 0.056

What is claimed is:

1. A method for the production of 2-butanol comprising:
a) providing a recombinant microbial production host cell comprising a nucleic acid molecule encoding a polypeptide having butanol dehydrogenase activity and a source of 2-butanone;
b) growing the microbial host cell of (a) under conditions whereby the nucleic acid molecule is expressed and the 2-butanone is converted to 2-butanol; and
c) optionally recovering the 2-butanol,
wherein the polypeptide having butanol dehydrogenase activity comprises an amino acid sequence that is at least 95% identical to the amino acid sequence of SEQ ID NO:2.

2. A method for the production of isobutanol comprising:
a) providing a recombinant microbial production host cell comprising a nucleic acid molecule encoding a polypeptide having butanol dehydrogenase activity and a source of isobutyraldehyde;
b) growing the microbial host cell of (a) under conditions whereby the nucleic acid molecule is expressed and the isobutyraldehyde is converted to isobutanol; and
c) optionally recovering the isobutanol
wherein the polypeptide having butanol dehydrogenase activity comprises an amino acid sequence that is at least 95% identical to the amino acid sequence of SEQ ID NO:2.

3. A method for the production of 1-butanol comprising
a) providing a recombinant microbial production host cell comprising a nucleic acid molecule encoding a polypeptide having butanol dehydrogenase activity and a source of butyraldehyde; and
b) growing the microbial host cell of (a) under conditions whereby the nucleic acid molecule is expressed and the butyraldehyde is converted to 1-butanol;
c) and optionally recovering the 1-butanol,
wherein the polypeptide having butanol dehydrogenase activity comprises an amino acid sequence that is at least 95% identical to the amino acid sequence of SEQ ID NO:2.

4. A method according to claim 1, 2 or 3 wherein the recombinant microbial host cell of (a) is selected from the group consisting of bacteria, cyanobacteria, filamentous fungi and yeast.

5. A method according to claim 4 wherein said recombinant microbial host cell is a member of a genus selected from the group consisting of *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula, Kluyveromyces* and *Saccharomyces*.

* * * * *